(12) United States Patent
Chen et al.

(10) Patent No.: US 11,460,293 B2
(45) Date of Patent: Oct. 4, 2022

(54) SURFACE QUALITY SENSING USING SELF-MIXING INTERFEROMETRY

(71) Applicant: Apple Inc., Cupertino, CA (US)

(72) Inventors: Tong Chen, Fremont, CA (US); Ahmet Fatih Cihan, San Jose, CA (US); Mingzhou Jin, Campbell, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/124,132

(22) Filed: Dec. 16, 2020

(65) Prior Publication Data

US 2022/0099436 A1 Mar. 31, 2022

Related U.S. Application Data

(60) Provisional application No. 63/083,431, filed on Sep. 25, 2020.

(51) Int. Cl.
*G01B 9/02097* (2022.01)
*G01B 11/30* (2006.01)
(Continued)

(52) U.S. Cl.
CPC ........ *G01B 11/303* (2013.01); *G01B 9/02092* (2013.01); *G01B 9/02094* (2013.01);
(Continued)

(58) Field of Classification Search
CPC ... G01B 11/303; G01B 11/2441; G01B 11/30; G01B 9/02092; G01B 9/02094; G01B 9/02097; A61B 5/0064; A61B 5/441
See application file for complete search history.

(56) References Cited

U.S. PATENT DOCUMENTS

| 4,254,333 A | 3/1981 | Bergström |
| 4,468,131 A | 8/1984 | Bui et al. |

(Continued)

FOREIGN PATENT DOCUMENTS

| CN | 102109650 | 6/2011 |
| CN | 108225543 | 6/2018 |

(Continued)

OTHER PUBLICATIONS

U.S. Appl. No. 11/156,456 filed Oct. 2021, Chen et al.
(Continued)

*Primary Examiner* — Jonathan M Hansen
(74) *Attorney, Agent, or Firm* — Brownstein Hyatt Farber Schreck, LLP

(57) ABSTRACT

An electronic device is described. The electronic device includes a housing, a set of one or more SMI sensors attached to the housing, and a processor. The set of one or more SMI sensors includes a set of one or more electromagnetic radiation emitters having a set of one or more resonant cavities and configured to emit a set of one or more beams of electromagnetic radiation. The set of one or more SMI sensors also includes a set of one or more detectors configured to generate indications of self-mixing within the set of one or more resonant cavities. The processor is configured to characterize, using the indications of self-mixing, an optical field speckle of a target. The processor is also configured to characterize, using the characterization of the optical field speckle, a surface quality of the target.

20 Claims, 15 Drawing Sheets

(51) Int. Cl.
  *G01B 9/02* (2022.01)
  *G01B 11/24* (2006.01)
  *A61B 5/00* (2006.01)

(52) U.S. Cl.
  CPC ...... *G01B 9/02097* (2013.01); *G01B 11/2441* (2013.01); *G01B 11/30* (2013.01); *A61B 5/0064* (2013.01); *A61B 5/441* (2013.01)

(56) References Cited

U.S. PATENT DOCUMENTS

| | | | |
|---|---|---|---|
| 6,233,045 B1 * | 5/2001 | Suni | G01P 3/366 356/5.1 |
| 6,816,523 B1 | 11/2004 | Glenn et al. | |
| 6,872,931 B2 | 3/2005 | Liess et al. | |
| 7,277,180 B2 | 10/2007 | Townley-Smith et al. | |
| 7,388,672 B2 | 6/2008 | Zhou et al. | |
| 7,509,050 B2 | 3/2009 | Ekkizogloy et al. | |
| 7,589,709 B2 | 9/2009 | Liess et al. | |
| 7,620,332 B2 | 11/2009 | Nishiyama | |
| 7,675,020 B2 | 3/2010 | Machida | |
| 7,995,193 B2 | 8/2011 | Kuwata | |
| 8,208,814 B2 | 6/2012 | Sheth et al. | |
| 8,446,592 B1 | 5/2013 | Arissian | |
| 8,529,460 B2 | 9/2013 | Kawano et al. | |
| 8,736,581 B2 | 5/2014 | Han et al. | |
| 8,751,091 B2 | 6/2014 | Moench et al. | |
| 8,781,687 B2 | 7/2014 | Han et al. | |
| 8,896,745 B2 | 11/2014 | Takachi | |
| 8,942,069 B2 | 1/2015 | Tortora | |
| 9,004,698 B2 | 4/2015 | Kilcher et al. | |
| 9,091,573 B2 | 7/2015 | Van Der Lee et al. | |
| 9,160,390 B2 | 10/2015 | Zhou et al. | |
| 9,648,221 B2 | 5/2017 | Seo et al. | |
| 9,726,474 B2 | 8/2017 | Royo Royo et al. | |
| 9,778,037 B2 | 10/2017 | Bestler | |
| 9,912,923 B2 | 3/2018 | Kilcher et al. | |
| 9,952,245 B2 | 4/2018 | Ueno | |
| 10,184,783 B2 | 1/2019 | Flanders et al. | |
| 10,215,555 B2 | 2/2019 | Chen et al. | |
| 10,317,651 B2 | 6/2019 | Furutake et al. | |
| 10,379,028 B2 | 8/2019 | Spruit et al. | |
| 10,386,554 B2 | 8/2019 | Hjelmstrom et al. | |
| 10,492,679 B2 | 12/2019 | Zhou | |
| 10,503,048 B2 | 12/2019 | Del Bino et al. | |
| 10,555,079 B2 | 2/2020 | Bakish | |
| 10,613,625 B2 | 4/2020 | Huang et al. | |
| 10,581,474 B1 | 6/2020 | Fishman et al. | |
| 10,718,922 B2 | 7/2020 | Yong et al. | |
| 10,791,283 B2 | 9/2020 | Bardagjy et al. | |
| 10,845,873 B2 | 11/2020 | Huang | |
| 10,871,820 B2 | 12/2020 | Mutlu et al. | |
| 11,150,332 B1 | 10/2021 | Chen et al. | |
| 11,157,113 B2 | 10/2021 | Winkler et al. | |
| 2005/0156874 A1 | 7/2005 | Kong | |
| 2005/0157971 A1 | 7/2005 | Juijve | |
| 2006/0239312 A1 | 10/2006 | Kewitsch et al. | |
| 2008/0123106 A1 * | 5/2008 | Zeng | G01N 21/47 356/600 |
| 2009/0002829 A1 | 1/2009 | Shinohara | |
| 2011/0116101 A1 * | 5/2011 | Werner | G01S 17/50 356/521 |
| 2011/0126617 A1 | 6/2011 | Bengoechea Apezteguia et al. | |
| 2011/0267467 A1 | 11/2011 | Kimura et al. | |
| 2012/0281221 A1 | 11/2012 | Studer et al. | |
| 2014/0293055 A1 | 10/2014 | Otsuka | |
| 2015/0309568 A1 | 10/2015 | Miki | |
| 2016/0021285 A1 | 1/2016 | Nadler et al. | |
| 2016/0153838 A1 * | 6/2016 | Bosch | G01B 9/02083 356/498 |
| 2017/0090599 A1 | 3/2017 | Kuboyama et al. | |
| 2017/0192133 A1 | 7/2017 | Murakami et al. | |
| 2017/0343817 A1 | 11/2017 | Bietry et al. | |
| 2017/0374261 A1 | 12/2017 | Teich et al. | |
| 2018/0081434 A1 | 3/2018 | Siddiqui et al. | |
| 2019/0317454 A1 | 10/2019 | Holenarsipur et al. | |
| 2019/0391539 A1 | 12/2019 | Perkins et al. | |
| 2020/0072740 A1 | 3/2020 | Venturini et al. | |
| 2020/0103274 A1 | 4/2020 | Garrett et al. | |
| 2020/0200522 A1 | 6/2020 | Huang et al. | |
| 2020/0309661 A1 | 10/2020 | Spruit et al. | |
| 2020/0370879 A1 | 11/2020 | Mutlu et al. | |
| 2021/0003385 A1 | 1/2021 | Tan et al. | |
| 2021/0011559 A1 | 1/2021 | Mutlu et al. | |
| 2021/0015350 A1 | 1/2021 | Butte et al. | |
| 2021/0116355 A1 | 4/2021 | Spruit et al. | |
| 2021/0294489 A1 | 9/2021 | Li et al. | |

FOREIGN PATENT DOCUMENTS

| | | |
|---|---|---|
| WO | WO 05/013517 | 2/2005 |
| WO | WO 09/156937 | 12/2009 |
| WO | WO 17/178711 | 10/2017 |
| WO | WO 18/036685 | 3/2018 |
| WO | WO 19/042953 | 3/2019 |

OTHER PUBLICATIONS

U.S. Appl. No. 16/418,875, filed May 21, 2019, Chen et al.
U.S. Appl. No. 16/773,827, filed Jan. 27, 2020, Mutlu et al.
U.S. Appl. No. 16/827,646, filed Mar. 23, 2020, Li et al.
U.S. Appl. No. 16/849,826, filed Apr. 15, 2020, Mutlu et al.
U.S. Appl. No. 16/917,891, filed Jun. 30, 2020, Chen et al.

* cited by examiner

SURFACE QUALITY SENSING USING SELF-MIXING INTERFEROMETRY

CROSS-REFERENCE TO RELATED APPLICATION

This application is a nonprovisional of and claims the benefit under 35 U.S.C. § 119(e) of U.S. Provisional Patent Application No. 63/083,431, filed Sep. 25, 2020, the contents of which are incorporated herein by reference as if fully disclosed herein.

FIELD

The described embodiments generally relate to the sensing of surface quality and, more particularly, to the sensing of surface quality using self-mixing interferometry.

BACKGROUND

Surface qualities such as roughness and waviness play a critical role in a person's physical interaction with, and perception of, real world objects. For example, an object having a rougher surface may generate more friction when a person touches, feels, or grabs the object. When trying to understand the surface quality of an object, a person may drag their finger along the object's surface. This may stimulate (e.g., vibrate) a large number of tactile receptors in the person's finger and give the person a good understanding of whether, and to what degree, the surface is rough or wavy. When grabbing an object, some amount of roughness may make it easier to hold onto the object, but too much roughness may cause pain and make it difficult to hold onto the object. When a person is painting, drawing, or writing on a rougher surface, some brushes, pens, or pencils (especially ones having softer or more flexible tips) may generate heavier strokes or strokes having more diffuse edges. When visible light passes through or is redirected from a smooth surface, an observer may be able to discern that the transmitted or redirected light has a specular response, which in turn can help the observer appreciate that the surface is smooth. When visible light passes through or is redirected from a rough surface, an observer may be able to discern that the transmitted or redirected light has a diffuse response, which in turn can help the observer appreciate that the surface is rough.

For a machine to better understand the objects that it images or contacts, the machine should ideally know, or be able to determine, the surface quality of the objects. When the machine knows the surface quality of an object, the machine can better represent the object on a display, model the interaction of a person or other (real or virtual) object with the object (e.g., in an augmented reality (AR) or virtual reality (VR) environment), describe or recreate the surface quality for a person who has not physically interacted with the object (e.g., via haptic, electrostatic, thermal, and/or other types of actuators), and so on.

Existing surface texture measurement systems may include, for example, a mechanical stylus profiler, a white light interferometric profiler (a type of image-based interferometric profiler), a laser confocal profiler, and so on.

SUMMARY

Embodiments of the systems, devices, methods, and apparatus described in the present disclosure use self-mixing interferometry (SMI) to sense surface quality. Described embodiments may include, for example, a single SMI sensor; a set of multiple SMI sensors having different angles of incidence, numerical apertures, working distances, polarizations, and/or emitted electromagnetic radiation wavelengths; or one or more SMI sensors that emit and/or receive electromagnetic radiation through a tunable set of optics.

An SMI sensor is defined herein as a sensor configured to generate electromagnetic radiation (e.g., light), emit the electromagnetic radiation from a resonant cavity (e.g., a resonant optical cavity), receive a returned portion of the electromagnetic radiation (e.g., electromagnetic radiation that reflects or scatters from a surface) back into the resonant cavity, coherently or partially coherently self-mix the generated and returned electromagnetic radiation within the resonant cavity, and produce an output indicative of the self-mixing (i.e., an SMI signal). The generated, emitted, and returned electromagnetic radiation may be coherent or partially coherent. In some examples, the electromagnetic radiation emitted by an SMI sensor may be generated by an electromagnetic radiation source such as a laser (e.g., a vertical-cavity surface-emitting laser (VCSEL), a vertical external-cavity surface-emitting laser (VECSEL), a quantum-dot laser (QDL), a quantum cascade laser (QCL), an edge-emitting laser (EEL), a horizontal cavity surface-emitting laser (HCSEL), a solid state laser (SSL), or a gas laser), or a light-emitting diode (LED) (e.g., an organic LED (OLED), a resonant-cavity LED (RC-LED), a micro LED (mLED), a superluminescent LED (SLED), or an edge-emitting LED), and so on. The generated, emitted, and returned electromagnetic radiation may include, for example, visible or invisible light (e.g., green light, red light, infrared (IR) light, ultraviolet (UV) light, and so on). The output of an SMI sensor (i.e., the SMI signal) may include a photocurrent produced by a photodetector (e.g., a photodiode), which photodetector is integrated with, or positioned under, above, or next to, the sensor's electromagnetic radiation source. Alternatively or additionally, the output of an SMI sensor may include a measurement of the current or junction voltage of the SMI sensor's electromagnetic radiation source.

In a first aspect, the present disclosure describes an electronic device. The electronic device may include a housing, a set of one or more SMI sensors attached to the housing, and a processor. The set of one or more SMI sensors may include a set of one or more electromagnetic radiation emitters having a set of one or more resonant cavities and configured to emit a set of one or more beams of electromagnetic radiation. The set of one or more SMI sensors may also include a set of one or more detectors configured to generate indications of self-mixing within the set of one or more resonant cavities. The processor may be configured to characterize, using the indications of self-mixing, an optical field speckle of a target. The processor may also be configured to characterize, using the characterization of the optical field speckle, a surface quality of the target.

In a second aspect, the present disclosure describes a method. The method may include receiving indications of self-mixing from a set of one or more SMI sensors; determining, using the indications of self-mixing, at least one of a distance or directional velocity with respect to a target; characterizing, using the indications of self-mixing and the at least one of the distance or directional velocity, an optical field speckle of the target; and characterizing, using the characterization of the optical field speckle, a surface quality of the target.

In a third aspect, a method of characterizing surface quality is described. The method may include receiving indications of self-mixing from a set of one or more SMI sensors; characterizing, using the indications of self-mixing, an optical field speckle of a target; and characterizing, using the characterization of the optical field speckle, a surface quality of the target.

In addition to the exemplary aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
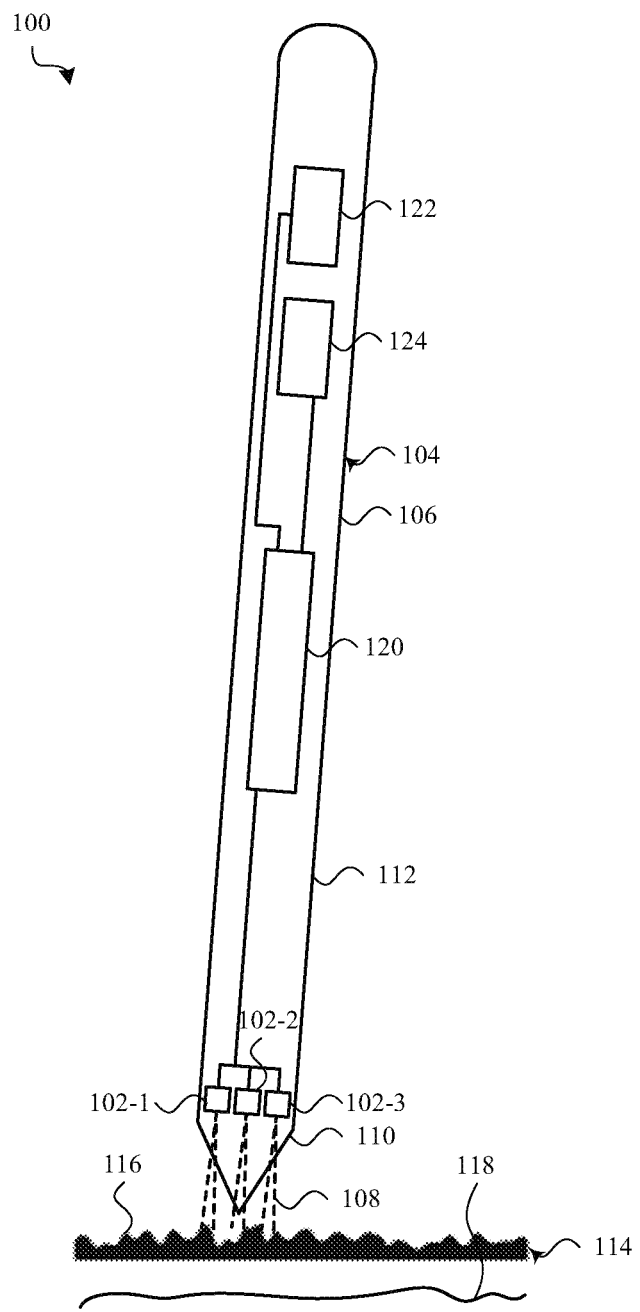
FIG. 1A shows an example of a stylus that includes a set of one or more SMI sensors.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following description relates to SMI-based surface quality sensing. The described embodiments may be less bulky (more compact), consume less power, and operate at a higher speed than existing mechanical surface profiles and/or image-based surface quality sensors, and in some cases may be compact enough to be incorporated into a device that can be comfortably held or worn, such as a stylus, glove, or ring. For example, a set of SMI sensors and processing system coupled thereto may be incorporated into a stylus (or electronic pen, pencil, or brush) that can be used to write, draw, or paint on any surface while rendering, on an associated electronic display, a line quality (or stroke) that corresponds to the surface quality (e.g., the roughness or waviness) of the surface on which the user is writing, drawing, or painting. As another example, a set of SMI sensors and an associated processing system may be incorporated into a glove that may sense the surface qualities of objects while the glove's user navigates an AR or VR environment. More generally, a set of SMI sensors and part or all of an associated processing system may be incorporated into any device that enables a machine (or computer) to sense a surface quality of a physical object. The device may in some cases contact the object to sense the surface quality, but in some cases need not.

As described herein, SMI sensors may generate SMI signals that may be used (e.g., analyzed) to characterize a statistical property (optical field speckle). The statistical property (optical field speckle) may then be used to characterize a physical property (surface quality).

The described SMI-based surface quality sensors can provide higher spatial resolution and dynamic range than image-based surface quality sensors, and may cost less, consume less power, and contemporaneously determine a device's posing (e.g., distance, velocity, and so on). The described SMI-based surface quality sensors can also function without a need for a predetermined surface quality (e.g., a glass screen, a special paper, or the like).

These and other systems, devices, methods, and apparatus are described with reference to FIGS. 1A-12. However, those skilled in the art will readily appreciate that the detailed description given herein with respect to these figures is for explanatory purposes only and should not be construed as limiting.

Directional terminology, such as "top", "bottom", "upper", "lower", "front", "back", "over", "under", "above", "below", "left", "right", etc. is used with reference to the orientation of some of the components in some of the figures described below. Because components in various embodiments can be positioned in a number of different orientations, directional terminology is used for purposes of illustration only and is in no way limiting. The directional terminology is intended to be construed broadly, and therefore should not be interpreted to preclude components being oriented in different ways. Also, as used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

FIG. 1A shows an example of a stylus 100 that includes a set of one or more SMI sensors 102. By way of example, the stylus 100 is shown to include a first SMI sensor 102-1, a second SMI sensor 102-2, and a third SMI sensor 102-3. The SMI sensors 102 may be attached to a housing 104. By way of example, the SMI sensors 102 are shown to be housed within the housing 104, and the SMI sensors 102 may emit and receive electromagnetic radiation through an exterior surface 106 of the housing 104. In some cases, the SMI sensors 102 may be mounted directly to the housing 104. In other cases, the SMI sensors 102 may be mounted on a shared substrate, or on individual substrates, and the substrate(s) may be attached to the housing 104. Alternatively, one or more of the SMI sensors 102 may be mounted on an exterior surface 106 of the housing 104 or may extend through an opening in the exterior surface 106 of the housing 104.

The SMI sensors 102 may emit and receive electromagnetic radiation 108 through the exterior surface 106 of the housing 104, or through openings in the housing 104. Alternatively, and when an SMI sensor 102 is mounted on the exterior surface 106 of the housing or extends through an opening in the exterior surface 106, the SMI sensor 102 may emit and receive electromagnetic radiation 108 without the electromagnetic radiation passing through the housing 104.

In some embodiments, the housing 104 may have a tip 110 that is optically transparent to at least the electromagnetic radiation wavelength(s) emitted by the SMI sensors 102. For example, the tip 110 may be visibly clear, or may be optically transparent to the electromagnetic radiation emitted by the SMI sensors 102 but visibly opaque. In some embodiments, the tip 110 may be formed of a different material than an adjacent portion of the housing 104. In some embodiments, the tip 110 may be a monolithic extension of a body portion 112 (i.e., a stylus body) of the housing 104. In some cases, the tip 110 may have a curved or arcuate exterior profile, as shown. In other cases, the tip 110 may have a tapered exterior profile that culminates at a point or around a flat end surface. The tip 110 may also have a squarish profile, faceted profile, or other profiles.

Figure 3:
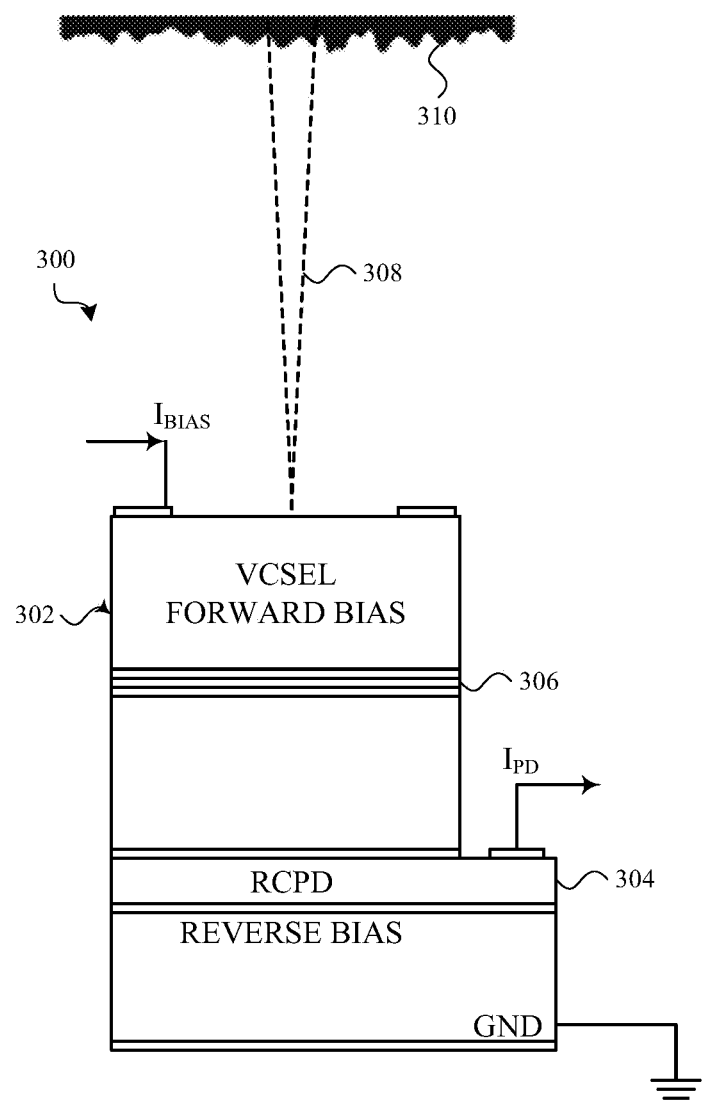
FIG. 3 shows an example SMI sensor.

The set of one or more SMI sensors 102 may include a set of one or more electromagnetic radiation sources having a set of one or more resonant cavities. The set of one or more resonant cavities may be configured to emit a set of one or more beams of electromagnetic radiation 108. The set of one or more SMI sensors 102 may also include a set of one or more detectors configured to generate indications of self-mixing within the set of one or more resonant cavities. The self-mixing may be coherent or partially coherent self-mixing of generated electromagnetic radiation and a returned portion (e.g., a scattered or reflected portion) of the emitted electromagnetic radiation 108. In some embodiments, the electromagnetic radiation source(s) may include one or more of a laser (e.g., a VCSEL, a VECSEL, a QDL, a QCL, an EEL, a HCSEL, an SSL, or a gas laser), or an LED (e.g., an OLED, an RC-LED, an mLED, a SLED, or an edge-emitting LED), and so on. The generated, emitted, and returned electromagnetic radiation may include, for example, visible or invisible light (e.g., green light, red light, IR light, UV light, and so on). The detector(s) may include one or more of a photodetector (e.g., a photodiode) that is integrated with, or positioned under, above, or next to, an SMI sensor's electromagnetic radiation source; a circuit configured to measure an electrical parameter (e.g., a current or junction voltage) of the SMI sensor's electromagnetic radiation source; and so on. The indications of self-mixing generated by the set of one or more detectors may include electrical signals, referred to herein as SMI signals, or digitized samples of the SMI signals. An example SMI sensor including a photodiode integrated with a VCSEL is shown in FIG. 3.

The beams of electromagnetic radiation 108 emitted by the SMI sensors 102 may scatter or reflect off of a target 114, and in some cases may scatter or reflect off of different surfaces or layers of the target 114. For example, depending on the optical transmissivities of an exterior surface 116 and one or more subsurfaces 118 (e.g., surfaces of layers or objects beneath the exterior surface 116) of the target 114, some or all of the emitted electromagnetic radiation 108 may scatter or reflect from the exterior surface 116, and other portions of the emitted electromagnetic radiation 108 may scatter or reflect from the one or more subsurfaces 118.

The exterior surface 116 (or a subsurface 118 of the target 114) may have a surface quality, which surface quality may be defined in terms of a surface roughness, a surface waviness, a refractive index, a subsurface scattering, and so on. When a beam of electromagnetic radiation 108 emitted by an SMI sensor 102 scatters or reflects off of the target 114, and a returned portion of the beam mixes with electromagnetic radiation generated by the SMI sensor, within a resonant cavity of the SMI sensor's electromagnetic radiation source, the SMI signal generated by the SMI sensor 102 may include information about the surface quality. This information may be used to characterize the surface quality.

A processing system 120 (i.e., a system including at least one processor) may be disposed within the housing 104, located in a remote device that is in communication with the stylus 100 via a wired or wireless interface, or distributed between the stylus 100 and a remote device. The processing system 120, or one or more processors thereof, may be configured to characterize an optical field speckle of the target 114. The optical field speckle may be characterized using the indications of self-mixing generated by the SMI sensors 102, and in some cases may be further characterized using a set of known relationships between the SMI sensors 102 and the tip 110, an output of a motion sensor 122, and so on. The processing system 120, or one or more processors thereof, may also be configured to characterize a surface quality of the target 114. The surface quality may be characterized using the characterization of the optical field speckle, and in some cases may be a quality of the exterior surface 116 and/or a subsurface 118 of the target 114.

In some embodiments, the processing system 120, or one or more processors thereof, may also use the indications of self-mixing to determine a spatial relationship between the housing 104 (or stylus 100, or tip 110) and the target 114, such as one or more of: a posing of the housing 104 (or stylus 100, or tip 110) with respect to the target 114; a distance of the housing 104 (or stylus 100, or tip 110) to the target 114; or a velocity of movement between the housing 104 (or stylus 100, or tip 110) and the target 114. The spatial relationship may be determined contemporaneously with characterizing the optical field speckle and/or characterizing the surface quality of the target 114. Alternatively, the spatial relationship may be determined before or after characterizing the optical field speckle and/or characterizing the surface quality of the target 114.

In some embodiments, the stylus 100 may include a motion sensor 122, which in some cases may take the form of one or more of an inertial sensor, one or more accelerometers, a gyroscope, and so on. An output or outputs of the motion sensor 122 may be used by the processing system 120, or a processor thereof, in conjunction with or instead of the indications of self-mixing generated by the set of one or more SMI sensors 102, to determine the posing of the housing 104 (or stylus 100, or tip 110) with respect to the target 114; the distance of the housing 104 (or stylus 100, or tip 110) to the target 114; or the velocity of movement between the housing 104 (or stylus 100, or tip 110) and the target 114.

In some embodiments, the stylus 100 may include one or more actuators 124, such as one or more haptic actuators and/or electrostatic actuators, for providing feedback to the user (or holder) of the stylus 100. In some cases, the feedback may be provided to the user in response to, or in an intensity that corresponds to, a surface quality sensed using the set of SMI sensors 102 and processing system 120. The actuators 124 may provide their feedback in response to one or more actuation signals provided by the processing system 120 or a processor thereof.

Figure 1B:
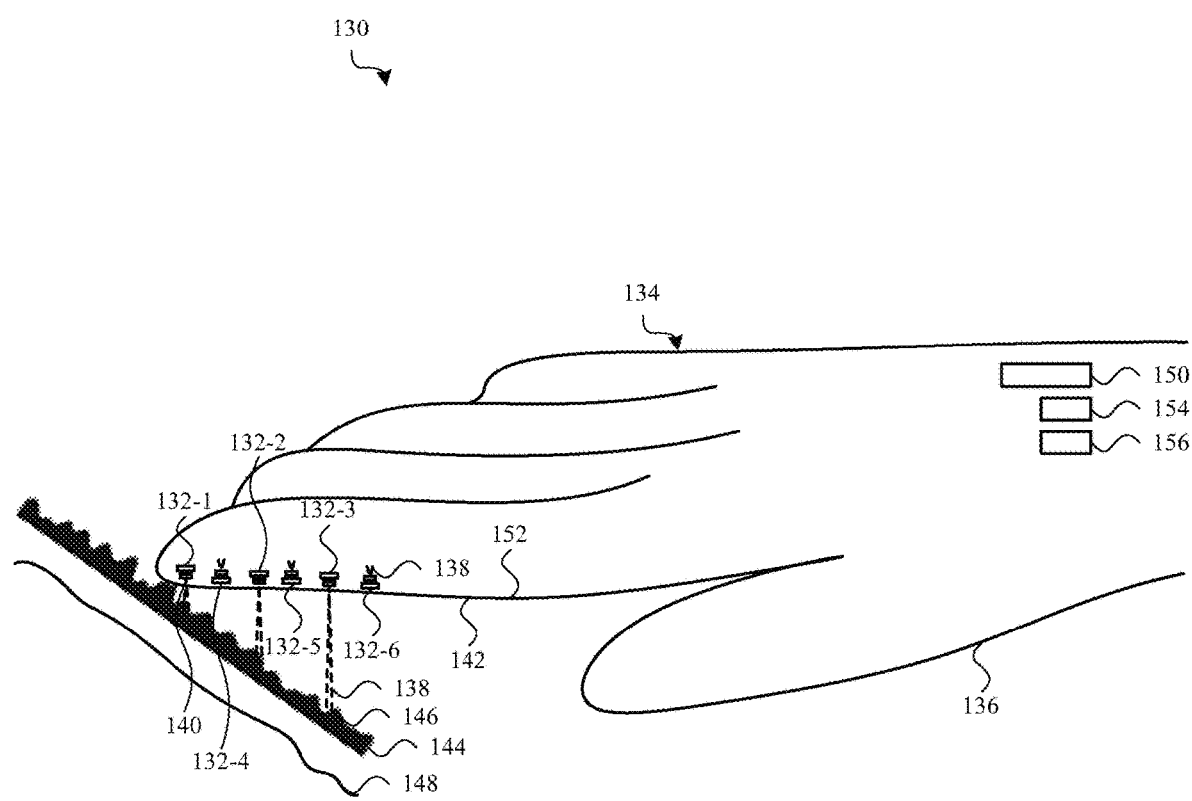
FIG. 1B shows an example of a wearable device that includes a set of one or more SMI sensors.

FIG. 1B shows an example of a wearable device 130 that includes a set of one or more SMI sensors 132. By way of example, the wearable device 130 is shown to be a glove that includes a first subset of SMI sensors (e.g., a first SMI sensor 132-1, a second SMI sensor 132-2, and a third SMI sensor 132-3) and/or a second subset of SMI sensors (e.g., a fourth SMI sensor 132-4, a fifth SMI sensor 132-5, and a sixth SMI sensor 132-6). In alternative embodiments, the wearable device 130 may be one or more of a synthetic skin (e.g., a fingertip skin), a ring, goggles or glasses, a helmet, a necklace, a belt, a shirt, and so on. The SMI sensors 132 may be attached to a housing 134, which in some cases may define exterior surfaces of the wearable device 130 and be formed of fabric, plastic, and/or other materials. By way of example, the SMI sensors 132 are shown to be housed within the housing 134, and the SMI sensors 132 may emit and receive electromagnetic radiation through the housing 134 (e.g., through an exterior surface 136 of the wearable device 130). In some cases, the SMI sensors 132 may be mounted directly to the housing 134. In other cases, the SMI sensors 132 may be mounted on a shared substrate (e.g., a flexible circuit substrate), or on individual substrates, and the substrate(s) may be attached to the housing 134. Alternatively, one or more of the SMI sensors 132 may be mounted on an exterior surface 136 of the housing 134 or may extend through an opening in the exterior surface 136 of the housing 134.

The SMI sensors 132 may emit and receive electromagnetic radiation 138 through the exterior surface 136 of the housing 134, or through openings in the housing 134. Alternatively, and when an SMI sensor 132 is mounted on the exterior surface 136 of the housing 134 or extends through an opening in the exterior surface 136, the SMI sensor 132 may emit and receive electromagnetic radiation 138 without the electromagnetic radiation passing through the housing 134.

In some embodiments, the housing 134 may have a portion or portions 140 that are optically transparent to at least the electromagnetic radiation wavelength(s) emitted by the SMI sensors 132. For example, the portion(s) 140 may be visibly clear, or may be optically transparent to the electromagnetic radiation emitted by the SMI sensors 132 but be visibly opaque. In some embodiments, the portion(s) 140 may be formed of a different material than adjacent portions of the housing 134. In some embodiments, the portion(s) 140 may be monolithic extensions of a body portion 142 of the housing 134.

The set of one or more SMI sensors 132 may be configured similarly to the SMI sensors described with reference to FIG. 1A, and may provide indications of self-mixing to a processing system 150 that includes one or more processors, as described with reference to FIG. 1A. The processing system 150, or one or more processors thereof, may be configured to characterize a surface quality of a target (e.g., a surface quality of an exterior surface 146 and/or subsurface 148 of the target 144; or a surface quality of the user's skin, internal to the wearable device 130). The processing system 150, or one or more processors thereof, may also or alternatively be configured to use the indications of self-mixing and/or one or more outputs of a motion sensor 156 to determine a spatial relationship between the housing 134 (or wearable device 130, or portion(s) 140) and the target 144 (or a spatial relationship between an interior surface of the housing 134 and its user).

The wearable device 130 may include the first subset of SMI sensors 132-1, 132-2, 132-3, the second subset of SMI sensors 132-4, 132-5, 132-6, and/or other subsets of SMI sensors. The first subset of SMI sensors may emit beams of electromagnetic radiation outward from the exterior surface 136 of the wearable device 130 (i.e., away from a user (or wearer) of the wearable device 130). For example, the first subset of SMI sensors may emit electromagnetic radiation outward from the fingertips of the user and function as a machine substitution for the user's own fingertips. In this manner, the first subset of SMI sensors may be used to characterize the surface quality of a remote target 144. The second subset of SMI sensors may emit beams of electromagnetic radiation inward from an interior surface 152 of the wearable device (i.e., toward the user of the wearable device 130 (e.g., toward the user's fingertips)). In this manner, the second subset of SMI sensors may be used to characterize the surface quality of a target (e.g., the user's skin) internal to the wearable device 130. The surface quality of a user's fingertip may be used to determine, for example, whether the user is pressing their fingertip against an object; is stretching the skin of their fingertip as they feel or grasp an object (e.g., straining); is hot or cold; is dry or damp (e.g., due to perspiration); and so on. The surface quality of a user's fingertip may also be used to uniquely identify the user's fingertip, as might be necessary when obtaining a biometric for user authentication.

In some embodiments, the wearable device 130 may include one or more actuators 154, such as one or more haptic actuators and/or electrostatic actuators, for providing feedback to the user (or wearer) of the wearable device 130. In some cases, the feedback may be provided to the user in response to, or in an intensity that corresponds to, a surface quality sensed using the set of SMI sensors 132 and processing system 150. The actuators 154 may provide their feedback in response to one or more actuation signals provided by the processing system 150 or a processor thereof.

Figure 2A:
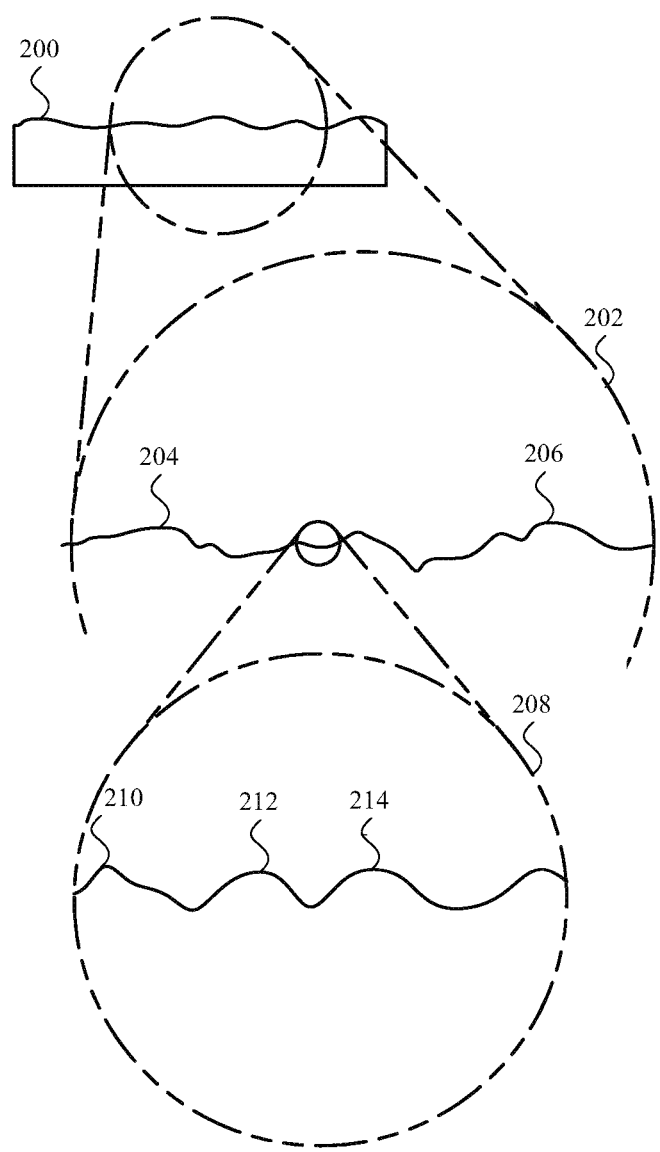
FIG. 2A shows example elevations of a surface having a surface roughness and a surface waviness.

FIG. 2A shows example elevations of a surface 200 having a surface roughness and a surface waviness. The surface roughness and/or surface waviness may be characterized using SMI-based sensing, and in some cases may be characterized using the set of one or more SMI sensors and processing system of the stylus or wearable device described with reference to FIG. 1A or 1B.

For purposes of this description, surface roughness and surface waviness are generally defined by the contour of a surface, but surface roughness has a higher spatial frequency variation in surface contour than surface waviness. Surface roughness may be used to characterize, for example, human skin, whereas surface waviness may be used to characterize, for example, the ridges and valleys of a fingerprint. As another example, surface roughness may be used to characterize the height/depth, width, and/or spacing of surface grains (i.e., grain height, grain depth, grain width, and/or grain spacing), and surface waviness may be used to characterize lower spatial frequency changes in the contour of a surface, as might be defined by different subsets of grains.

FIG. 2A shows a surface 200 having a surface roughness and a surface waviness. A first magnification 202 of the surface 200 illustrates larger features 204, 206 of the surface 200, which larger features 204, 206 may be identified using SMI-based sensing, and analyzed to characterize a surface waviness of the surface 200. A second (and greater) magnification 208 of the surface 200 illustrates smaller features 210, 212, 214 of the surface 200, which smaller features 210, 212, 214 may also be identified using SMI-based sensing, and analyzed to characterize a surface roughness of the surface 200.

Figure 2B:
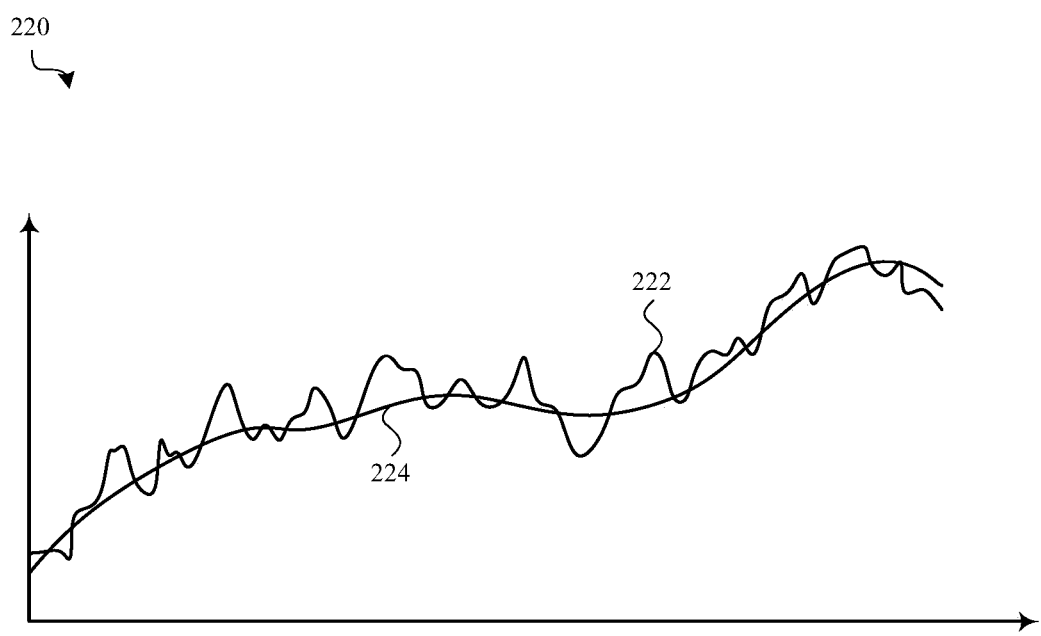
FIG. 2B shows an example graph of surface roughness and surface waviness for the surface shown in FIG. 2A.

FIG. 2B shows an example graph 220 of surface roughness and surface waviness, as determined from indications of self-mixing within a resonant cavity of at least one SMI sensor as a device including the at least one SMI sensor is drug across the surface 200 described with reference to FIG. 2A while the SMI sensor is emitting a beam of electromagnetic radiation toward the surface 200. As shown, surface roughness 222 may be represented by the raw SMI signal envelope variation. In contrast, surface waviness 224 may be represented by a target distance variation.

Surface roughness or surface waviness may be characterized, for example, in terms of a root-mean-square (RMS) surface roughness, $R_q$, an arithmetic mean deviation, $R_a$, and/or an RMS surface slope, $R\Delta_q$, where:

$$R_q = \sqrt{\frac{1}{L}\int_x Z(x)^2 dx};$$

$$R_a = \frac{1}{L}\int_x |Z(x, y)| dx;$$

and $$R\Delta_q = \sqrt{\frac{1}{L}\int_x \left(\frac{\partial Z(x)}{\partial x}\right)^2 dx}.$$

Figure 2C:
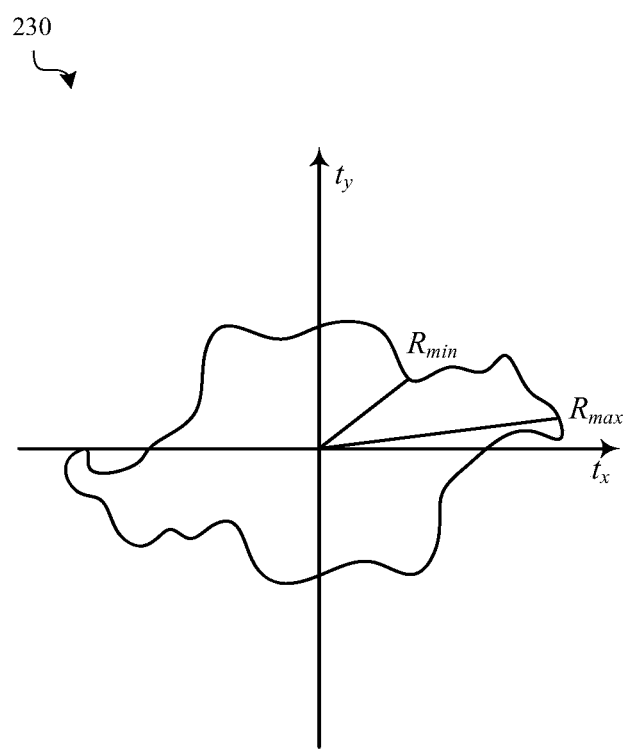
FIG. 2C shows an example lateral data distribution from which lateral correlation of surface texture may be determined for the surface shown in FIG. 2A.

FIG. 2C shows an example lateral data distribution 230 from which a lateral correlation (x-y correlation) of surface texture may be determined for the surface shown in FIG. 2A. The lateral correlation may also be determined from the indications of self-mixing.

Lateral correlation may be characterized, for example, in terms of correlation length, Sal, and texture aspect ratio, Str. Correlation length is a measure of the minimum spacing, $R_{min}$, between maximum heights of adjacent surface grains (i.e., Sal=$R_{min}$). Texture aspect ratio is a ratio of $R_{min}$ and $R_{max}$, such that $$Str = \frac{R_{min}}{R_{max}}.$$

Both $R_{min}$ and $R_{max}$ can be determined using the autocorrelation function:

$$f_{ACF}(t_x, t_y) = \frac{\int_x \int_y Z(x, y) Z(x-t_x, y-t_y) dy dx}{\int_x \int_y Z(x, y)^2 dy dx}$$

FIG. 3 shows an example SMI sensor 300 that may be used in one or more of the systems, devices, methods, or apparatus described herein. The example SMI sensor 300 includes a VCSEL 302 with an integrated resonant cavity (or intra-cavity) photodetector (RCPD) 304. The resonant cavity 306 may be bounded by a pair of distributed Bragg reflectors, with one of the distributed Bragg reflectors allowing a beam of electromagnetic radiation 308 to be emitted from the resonant cavity 306.

When the emitted beam of electromagnetic radiation 308 scatters or reflects from a target 310, a portion of the emitted beam may be returned toward the VCSEL 302 and re-enter the resonant cavity 306. Within the resonant cavity 306, the returned portion of the beam self-mixes with the electromagnetic radiation generated by the VCSEL 302 and alters various properties of the VCSEL 302. The altered properties include altered optical properties, which may be detected by the RCPD 304 and converted into an electrical signal (an SMI signal). The altered properties also include altered electrical properties, such as an altered current of a voltage-driven VCSEL 302, or an altered junction voltage of a current-driven VCSEL 302. Alternatives to the SMI sensor 300 may include a photodetector positioned above, below, or adjacent a VCSEL, or a circuit to measure a varying current or junction voltage of a VCSEL.

Figure 4A:
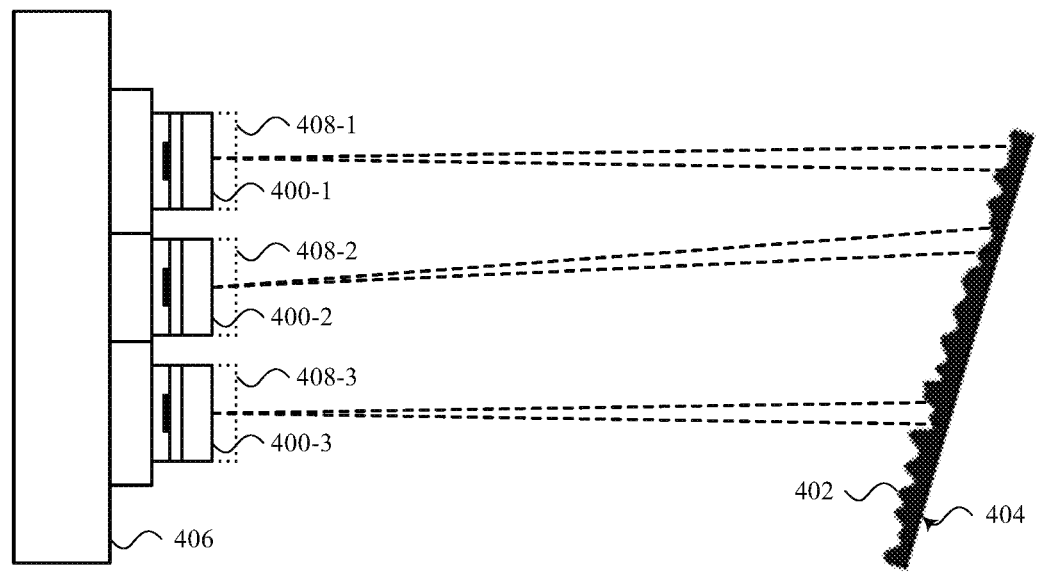
FIG. 4A shows an example array of SMI sensors in relation to a surface of a target.

FIG. 4A shows an example array of SMI sensors 400 in relation to a surface 402 of a target 404. By way of examples, the array of SMI sensors 400 is shown to include a first SMI sensor 400-1, a second SMI sensor 400-2, and a third SMI sensor 400-3. In alternative embodiments, the array of SMI sensors 400 may include more or fewer SMI sensors. Each of the SMI sensors 400-1, 400-2, 400-3 may be implemented as described with reference to FIG. 3 or in other ways. In some cases, the array of SMI sensors 400 may provide some or all of the SMI sensors included in the stylus or wearable device described with reference to FIG. 1A or 1B.

Each of the SMI sensors 400-1, 400-2, 400-3 may have different properties. For example, different ones of the SMI sensors 400-1, 400-2, 400-3 may have different angles of incidence (AOIs, where an AOI is an angle between an axis of an emitted beam of electromagnetic radiation with respect to a reference common to all of the SMI sensors, such as a planar target), different numerical apertures (NAs), different working distances (WDs), different polarizations, different scanning plans, and/or different emitted electromagnetic radiation wavelengths. The different properties of the SMI sensors 400-1, 400-2, 400-3 provide optical diversity for the different measurement channels provided by the SMI sensors 400-1, 400-2, 400-3, and may enable a processor or processing system that receives indications of self-mixing from the array of SMI sensors 400 to distinguish a greater range of surface qualities and/or a greater range of surface quality characteristics. Some of the above differences or diversities—e.g., AOI, NA, or polarization, and so on—can be achieved by the configurations of the SMI sensors themselves and/or by shared or individual external optics (e.g., optional individual external optics 408-1, 408-2, and/or 408-3).

The different SMI sensors 400-1, 400-2, 400-3 may be mounted on a common substrate 406 as shown (e.g., on a common printed circuit board (PCB), on a common flexible circuit substrate, or on a common semiconductor die in which the SMI sensors 400-1, 400-2, 400-3 are individually addressable). Alternatively, different SMI sensors may be mounted on different substrates.

Figure 4B:
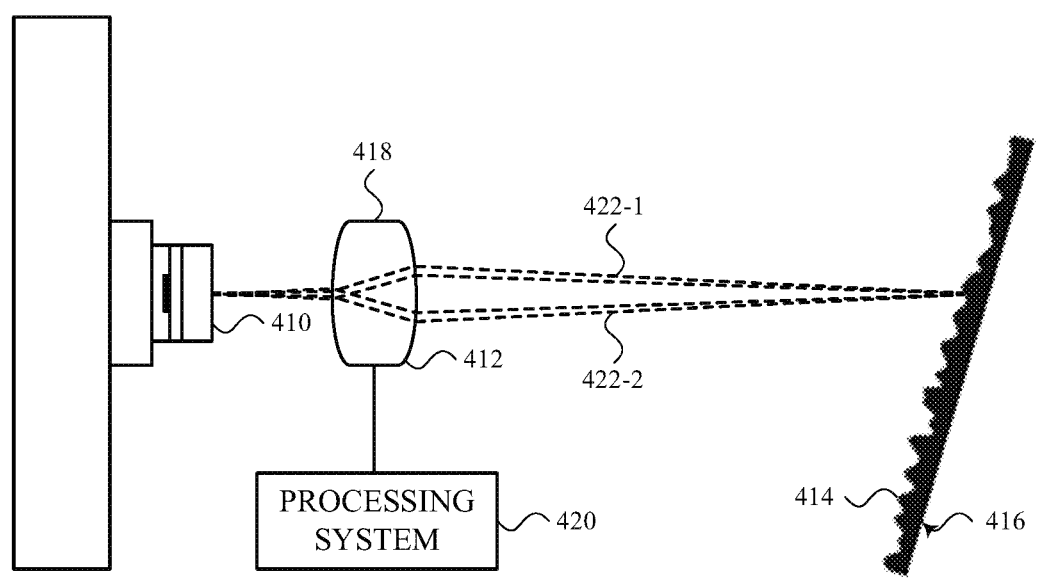
FIG. 4B shows an example SMI sensor and tunable set of optics in relation to a surface of a target.

FIG. 4B shows an example SMI sensor 410 and set of optics 412 in relation to a surface 414 of a target 416. The SMI sensor 410 may be implemented as described with reference to FIG. 3 or in other ways. In some cases, the SMI sensor 410 may provide one of the SMI sensors (or the only SMI sensor) included in the stylus or wearable device described with reference to FIG. 1A or 1B.

The set of optics 412 may be disposed over the SMI sensor 410, in an optical path of a beam of electromagnetic radiation 418 emitted by the SMI sensor 410. In some cases, the set of optics 412 may also be disposed over other SMI sensors (i.e., in the optical paths of the beams of electromagnetic radiation emitted by one or more other SMI sensors).

In some embodiments, the set of optics 412 may be a tunable set of optics. A processing system 420, processor thereof, or other circuit may be used to tune the set of optics 412. Tuning the set of optics 412 may provide diversity for the indications of self-mixing generated by the SMI sensor 410. Tuning the set of optics 412 may change, for example, the AOI, WD, and/or polarization of the emitted beam of electromagnetic radiation 418. The different tunable properties of the set of optics 412 may provide optical diversity for different measurement channels provided by the SMI sensor 410, and may enable a processor or processing system that receives indications of self-mixing from the SMI sensor 410 to distinguish a greater range of surface qualities and/or a greater range of surface quality characteristics.

In some embodiments, the set of optics 412 may include a reciprocal beam splitter, such as a fiber coupler, diffractive optical element, partial reflector, and so on. In these embodiments, the optical paths 422-1, 422-2 are reciprocal, such that multiple combinations of roundtrip paths having different AOI, WD, and/or polarization, and so on, can be re-mixed back to the SMI sensor 410.

In some embodiments, the set of optics 412 may include an optical circulator (i.e., a device having three or more optical ports), such as a birefringent optical circulator. The SMI sensor 410 may emit a beam of electromagnetic radiation 418 from a resonant cavity and into the set of optics 412, and receive a returned portion of the beam of electromagnetic radiation from the set of optics 412 and into the resonant cavity. Because of the optical circulator, the emitted beam of electromagnetic radiation 418 and returned portion of the beam of electromagnetic radiation may have non-reciprocal optical paths 422-1, 422-2 through the set of optics 412. The non-reciprocal paths may increase the diversity of the indications of self-mixing generated by the SMI sensor 410, and in some cases can be used for subsurface quality sensing. In some embodiments, the set of optics 412 may be tunable to alternatively provide reciprocal or non-reciprocal emission and reception optical paths through the set of optics 412.

Figure 5:
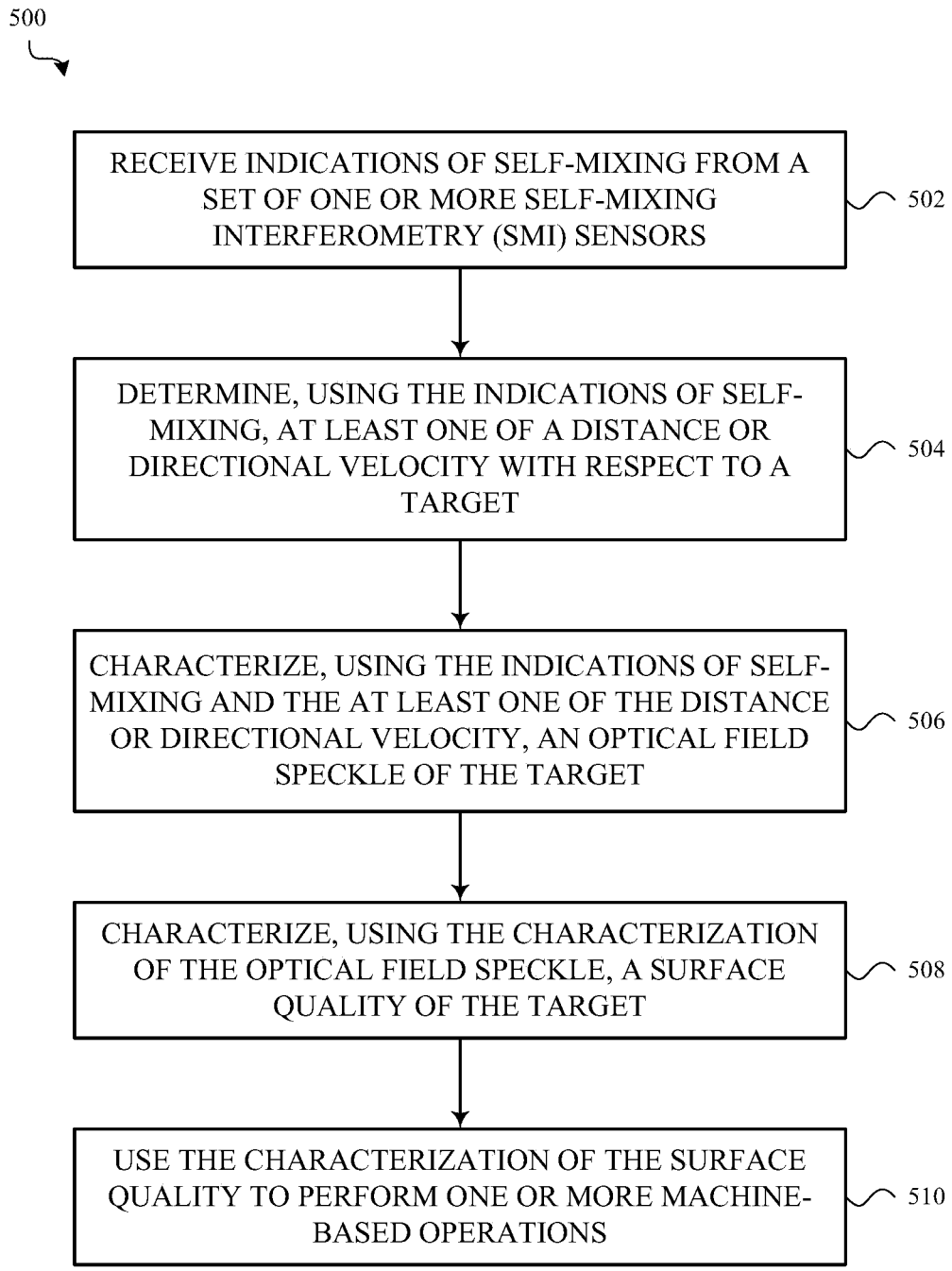
FIG. 5 shows an example method of characterizing a surface quality.

FIG. 5 shows an example method 500 of characterizing a surface quality. The method 500 may be performed, for example, by a set of one or more SMI sensors in combination with a processing system or processor. The set of one or more SMI sensors and processing system or processor may include any of the SMI sensors and processing systems (or processors) described herein.

At block 502, the method 500 may include receiving indications of self-mixing from a set of one or more SMI sensors.

At block 504, the method 500 may include determining, using the indications of self-mixing, at least one of a distance or directional velocity with respect to a target.

At block 506, the method 500 may include characterizing, using the indications of self-mixing and the at least one of the distance or directional velocity, an optical field speckle of the target. The optical field speckle may by characterized, for example, in terms of an optical field speckle contrast, a phase shift, and/or an optical field speckle correlation length At block 508, the method 500 may include characterizing, using the characterization of the optical field speckle, a surface quality of the target.

At block 510, the method 500 may include using the characterization of the surface quality to perform one or more machine-based operations. In some embodiments, the operations may include rendering a stroke on a display in accord with the surface quality. For example, the surface quality may be used to render a stroke made by a stylus that includes the set of one or more SMI sensors. The stroke may be rendered, for example, on an electronic display of a computer, mobile device, or wearable device. In some cases, the stroke may be a stroke of an alphanumeric character, electronic drawing, or electronic painting. The stroke may be rendered in accord with the surface quality, with appropriately sharp or diffuse edges, as determined by the characteristics of the surface quality as well as the type of brush, pen, or pencil that the stylus is simulating. Alternatively or additionally, the operations may include indicating, to a user, what type of surface they are writing or drawing on (e.g., a glossy surface, a matte surface, and so on).

In some embodiments, the operations at block 510 may include animating, in an AR or VR environment, an interaction between a virtual object and the target. The animating may be performed responsive to the surface quality of the target. For example, in an AR or VR environment that depicts a virtual balloon on a display, the AR or VR environment may animate a "popping" of the balloon if 1) the balloon virtually comes into contact with the target, and 2) the surface quality of the target is rough enough that it would typically cause the balloon to pop.

In some embodiments, the operations at block 510 may include causing an actuator to provide, to a user, feedback indicative of the surface quality. For example, a haptic actuator and/or electrostatic actuator of the stylus or wearable device described with reference to FIG. 1A or 1B may be caused to provide haptic and/or electrostatic feedback to a user of the stylus or wearable device.

In some embodiments, the operations at block 510 may include causing an actuator to provide, to a user, feedback that masks the surface quality. For example, destructive feedback may be provided to mask the vibrations of a sensed surface quality.

Figure 6:
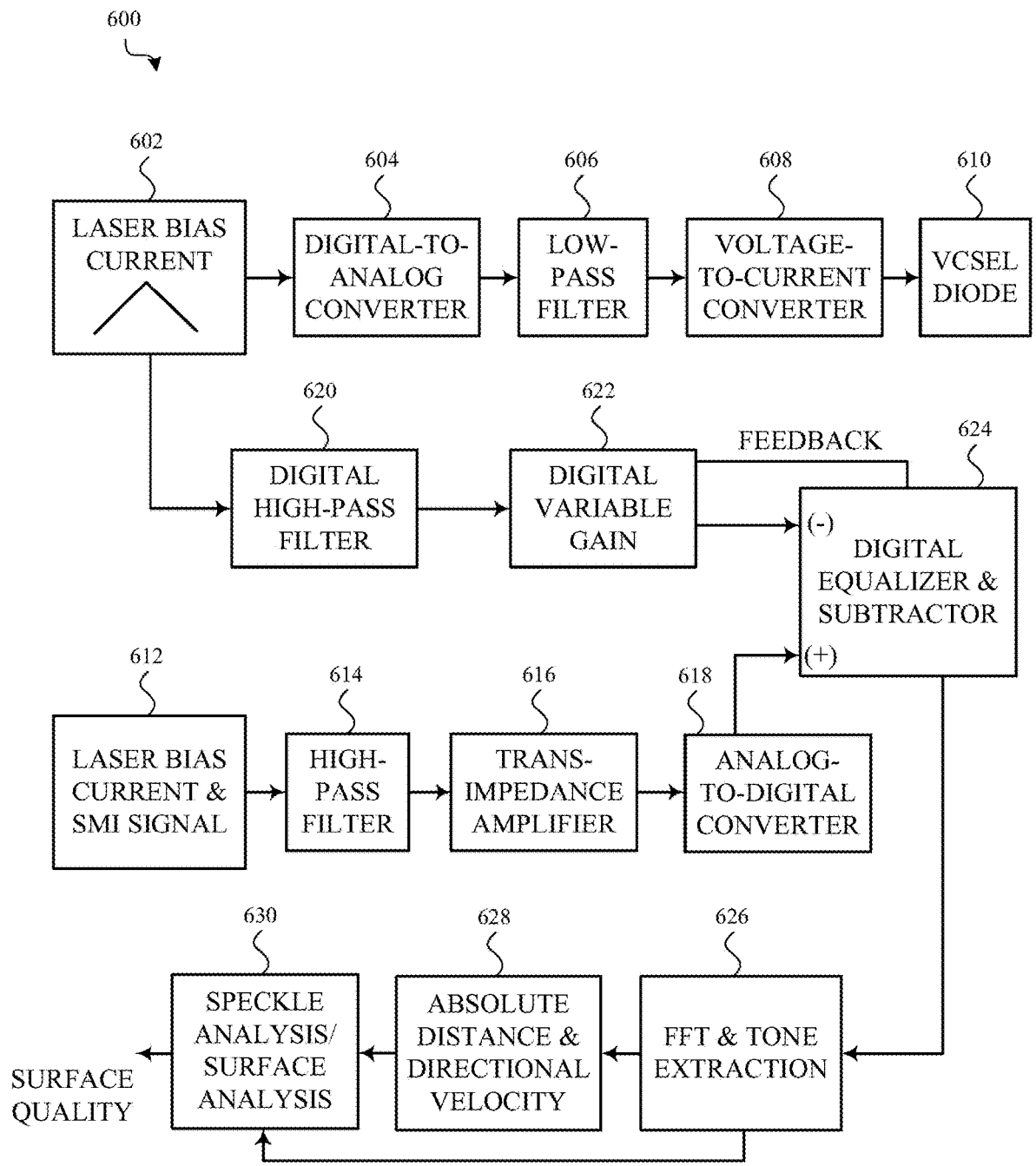
FIG. 6 shows an example method of operating an SMI sensor.

FIG. 6 shows an example method 600 of operating an SMI sensor, which in some cases may be one of the SMI sensors described herein. In accordance with the method 600, a system may generate an initial digital signal and process the digital signal to produce a triangle-modulated laser bias current 602. In an illustrated example, an initial step signal may be produced by a digital generator to approximate a triangle function (e.g., the triangle-modulated laser bias current 602). The triangle-modulated laser bias current 602 may be input to a digital-to-analog (DAC) converter 604. The resulting voltage signal may then be filtered by a low-pass filter 606 to remove quantization noise. Alternatively, an analog signal generator may be used to generate an equivalent triangle voltage signal directly. The filtered voltage signal may be input to a voltage-to-current converter 608 before the triangle-modulated laser bias current is used to bias the VCSEL diode 610.

As described above, scatter or reflections from a target may trigger self-mixing of electromagnetic radiation within the VCSEL diode 610. The self-mixing results in an altered operational parameter of the VCSEL diode 610. The altered parameter may be measured or inferred, either from an operational parameter of the VCSEL diode 610 or from an operational parameter of an associated photodetector. These alterations may be measured to produce a signal 612 (e.g., a combination of the triangle-modulated laser bias current 602 and a self-mixing signal). The signal 612 may have been measured by a photodetector and may be a triangle wave combined with a smaller and higher frequency signal related to the altered operational parameter of VCSEL diode 610.

The signal 612 may be passed through a high-pass filter 614, which may convert the major ascending and descending ramp components of the signal 612 to DC offsets. As the signal 612 may be a current signal generated by a photodetector, a trans-impedance amplifier 616 may produce a corresponding voltage output for further processing.

The voltage output of the trans-impedance amplifier 616 may be sampled and quantized by an analog-to-digital converter (ADC) 618. Before immediately applying a digital fast Fourier transform (FFT) to the output of the ADC 618, an equalization may be applied in order to clear remaining residue of the triangle signal received by the photodiode, thus isolating the interferometric signal. The initial digital signal values from the digital generator used to produce the triangle-modulated laser bias current 602 may be used as an input to a digital high-pass filter 620 to produce a digital signal to correspond to the output of the ADC 618. An adjustable gain may be applied by a digital variable gain circuit 622 to the output of the digital high-pass filter 620.

The output of the digital variable gain circuit 622 may be used as one input to the digital equalizer and subtractor 624. The other input to the digital equalizer and subtractor 624 may be the output of the ADC 618. The two signals may be subtracted and used as feedback to adjust a gain provided by the digital variable gain circuit 622.

Once a sufficient correlation is obtained by the feedback, an FFT and tone extraction circuit 626 may apply an FFT to the output of the digital equalizer and subtractor 624 (i.e., to indications of self-mixing). From the FFT spectra obtained, displacement or movement of the target (e.g., an absolute distance and directional velocity) may be inferred as indicated by block 628. During the FFT and tone extraction circuit 626 step, processing electronics performing portions of the method 600 may perform a spectrum analysis (e.g., a frequency domain analysis) on the signal received from the digital equalizer and subtractor 624. The spectrum analysis may isolate signals corresponding to changes in the operational parameter of the VCSEL diode 610 and may be used to measure real-world events (e.g., a distance between a target and the VCSEL diode 610, a speed of the target or the VCSEL diode 610, and so on). A time domain analysis of the indications of self-mixing may also be performed at block 626.

Outputs of the FFT and tone extraction circuit 626, and in some cases the absolute distance and directional velocity referenced in block 628, may be used as described herein to characterize an optical field speckle (e.g., perform a speckle analysis) at block 630, and further characterize a surface quality (e.g., perform a surface analysis) at block 630.

Figure 7A:
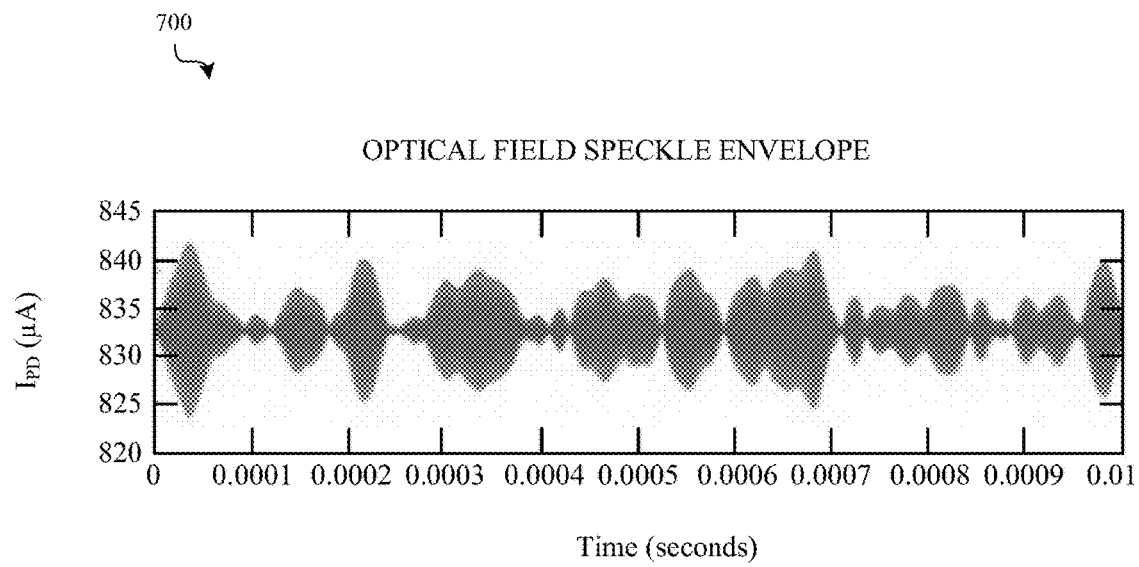
FIG. 7A shows an example optical field speckle envelope.

FIG. 7A shows an example optical field speckle envelope 700. The optical field speckle envelope 700 may be defined by the amplitude of an SMI signal as a beam of electromagnetic radiation emitted by an SMI sensor is scanned over a surface of a target. The SMI sensor may be any of the SMI sensors described herein.

Figure 7B:
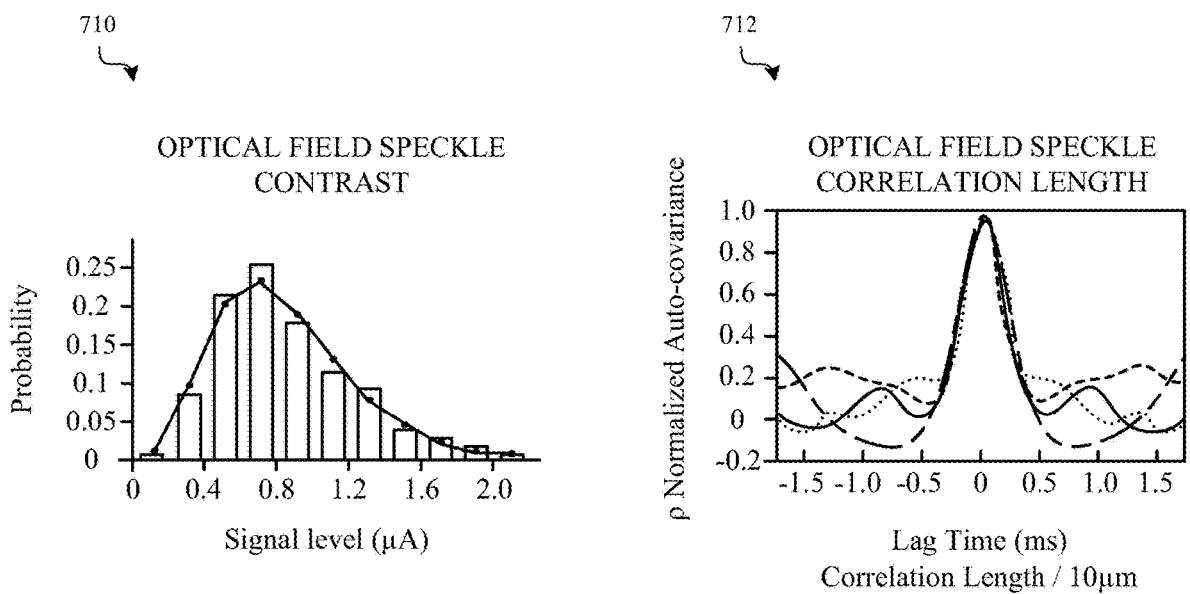
FIG. 7B shows example graphs of optical field speckle contrast and optical field speckle correlation.

FIG. 7B shows example graphs of optical field speckle contrast 710 and optical field speckle correlation length 712, which may be based on data obtained at blocks 626, 628, and 630 of FIG. 6 (and more specifically, based on the spectral analysis of temporal data shown in FIG. 7A). The optical field speckle contrast is a computed distribution of the amplitude of the optical field speckle envelope 700, and can be used to determine the standard deviation and other characteristics of the optical field speckle. In some cases, speckle correlation length can be calculated from autocorrelation of temporal data and converted into a spatial (length) unit using a measured target velocity.

The data shown in FIGS. 7A and 7B may be derived from indications of self-mixing for a single SMI sensor that provides a single measurement channel, or for each of multiple measurement channels (provided by a single or multiple SMI sensors). When the data is determined for multiple measurement channels, each measurement channel may be diverse from other measurement channels in terms of AOI, NA, WD, polarization, and/or emitted electromagnetic radiation wavelengths, for example.

Figure 8A:
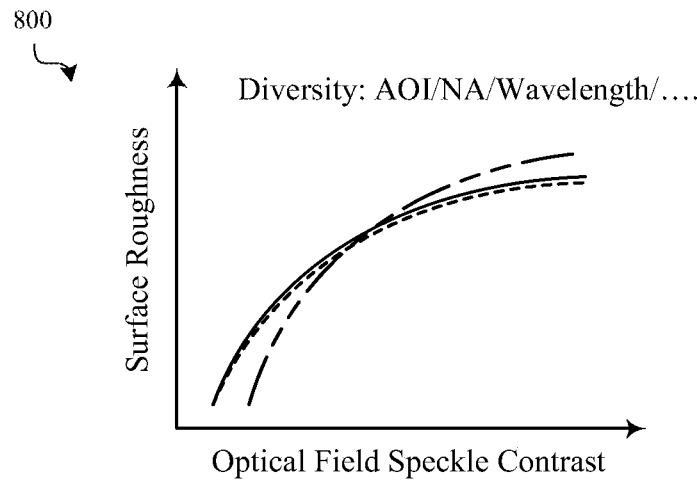
FIG. 8A shows an example relationship between optical field speckle contrast and surface roughness.
Figure 8B:
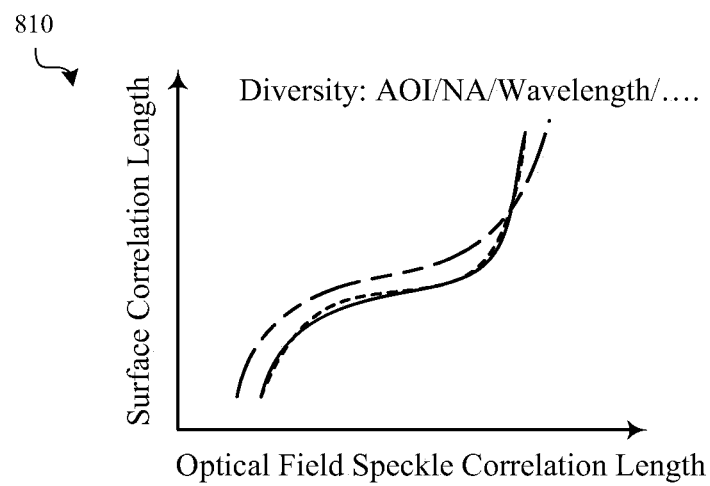
FIG. 8B shows an example relationship between optical field speckle correlation and surface correlation length.
Figure 8C:
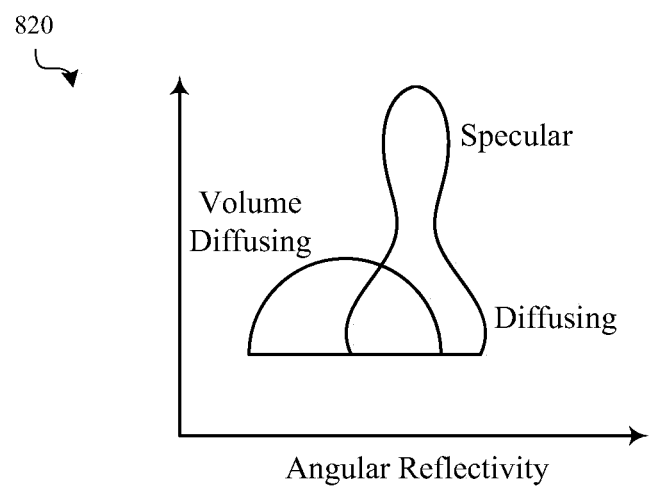
FIG. 8C shows an example use of optical field speckle characteristics to model angular reflectivity of a surface.

FIGS. 8A-8C show example correlations between characteristics of optical field speckle (i.e., optical characteristics of a surface) and characteristics of surface quality (i.e., physical characteristics of the surface). For example, FIG. 8A shows an example relationship 800 between optical field speckle contrast and surface roughness for SMI sensors having diverse parameters (e.g., different AOI/NA/Wavelength/ . . . ). As shown, optical field speckle contrast may not have a monotonic relationship with surface roughness, but it does have a defined relationship.

FIG. 8B shows an example relationship 810 between optical field speckle correlation length and surface correlation length for SMI sensors having diverse parameters (e.g., different AOI/NA/Wavelength/ . . . ). As shown, optical field speckle correlation may not have a monotonic relationship with surface correlation length, but it does have a defined relationship.

FIG. 8C shows an example use of optical field speckle characteristics to model angular reflectivity 820 of a surface. As shown, the angular reflectivity of a surface may be characterized as specular, diffusing, or volume diffusing, depending on the distribution of optical field speckle data.

Figure 9:
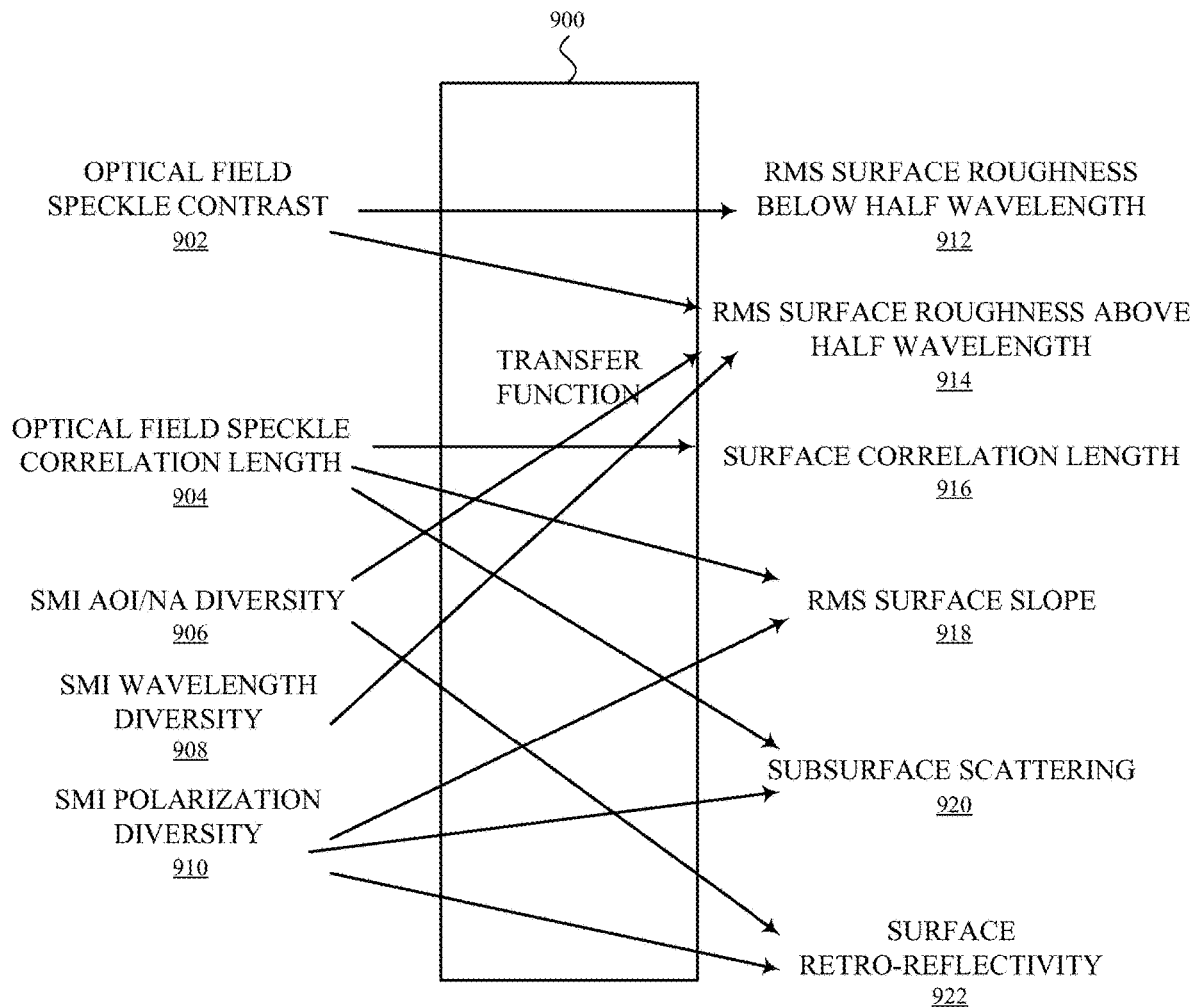
FIG. 9 shows an example transfer function for deriving surface quality characteristics from optical field speckle characteristics and indications of diversity in SMI sensor parameters.

FIG. 9 shows an example transfer function 900 for deriving surface quality characteristics from optical field speckle characteristics and indications of diversity in SMI sensor parameters. On the left side of the transfer function 900, optical field characteristics such as optical field speckle contrast 902 and optical field speckle correlation length 904 are provided as inputs to the transfer function. Also provided as inputs to the transfer function 900 are indications of diversity in SMI sensor parameters, such as SMI AOI/NA diversity 906, SMI wavelength diversity 908, and SMI polarization diversity 910. Additional or alternative optical field speckle characteristics and/or indications of diversity may also be provided as inputs to the transfer function 900.

On the right side of the transfer function 900, surface quality characteristics are shown as outputs of the transfer function. The surface quality characteristics may include, for example, an RMS surface roughness below a half wavelength 912, an RMS surface roughness above a half wavelength 914, a surface correlation length 916, an RMS surface slope 918, a subsurface scattering 920, and a surface retro-reflectivity 922. Additional or alternative surface quality characteristics may also be provided as outputs of the transfer function 900. A deterministic or statistical transfer function can be established between left and right sides of the transfer function 900, through regression, machine learning, and so on. For a statistical transfer function, the outputs on the right side may be associated with both a value and a probability.

As shown, some inputs to the transfer function 900 may influence some outputs of the transfer function 900 more than others, as shown by the arrows that map inputs of the transfer function 900 to outputs of the transfer function 900. However, any of the inputs may affect any of the outputs to some degree (though not always to a statistically significant degree).

Figure 10:
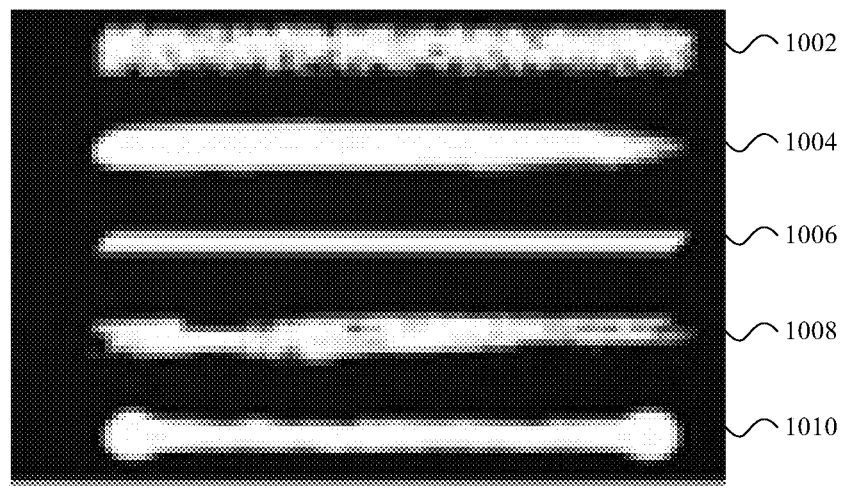
FIG. 10 shows an example set of stroke types.

FIG. 10 shows an example set of stroke types 1000 that may be rendered in accord with a surface quality sensed using a set of one or more SMI sensors. For example, depending on the surface quality sensed using a set of one or more SMI sensors, a processing system may render a stroke as a first stroke 1002 when the surface quality is a first surface quality, or as a second stroke 1004 when the surface quality is a second surface quality, or as a third stroke 1006 when the surface quality is a third surface quality, or as a fourth stroke 1008 when the surface quality is a fourth surface quality, or as a fifth stroke 1010 when the surface quality is a fifth surface quality.

Figure 11A:
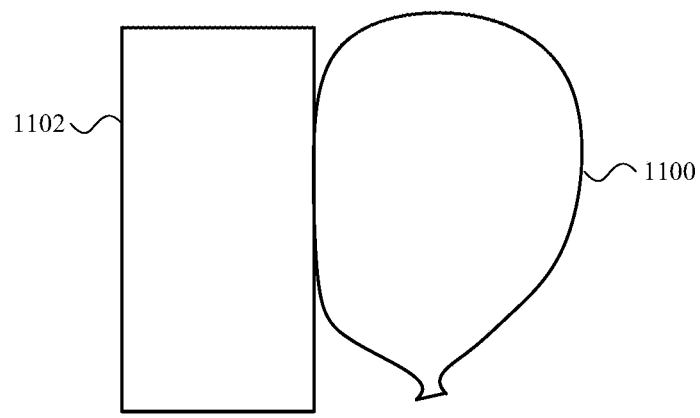
FIGS. 11A and 11B show alternative animations of a virtual object, which animations are responsive to a surface quality of a target.
Figure 11B:
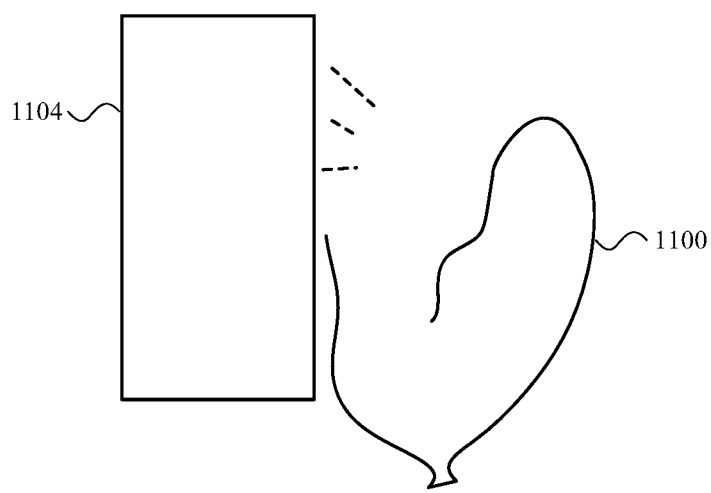

FIGS. 11A and 11B show alternative animations of a virtual object, which animations are responsive to a surface quality of a target. For example, FIG. 11A shows a virtual balloon 1100, in an AR environment, deflecting from a physical object 1102 that a processing system has determined to have a relatively smooth surface quality. In contrast, FIG. 11B shows the virtual balloon 1100 popping when the virtual balloon 1100 contacts a physical object 1104 that the processing system has determined to have a sufficiently rough surface quality.

Figure 12:
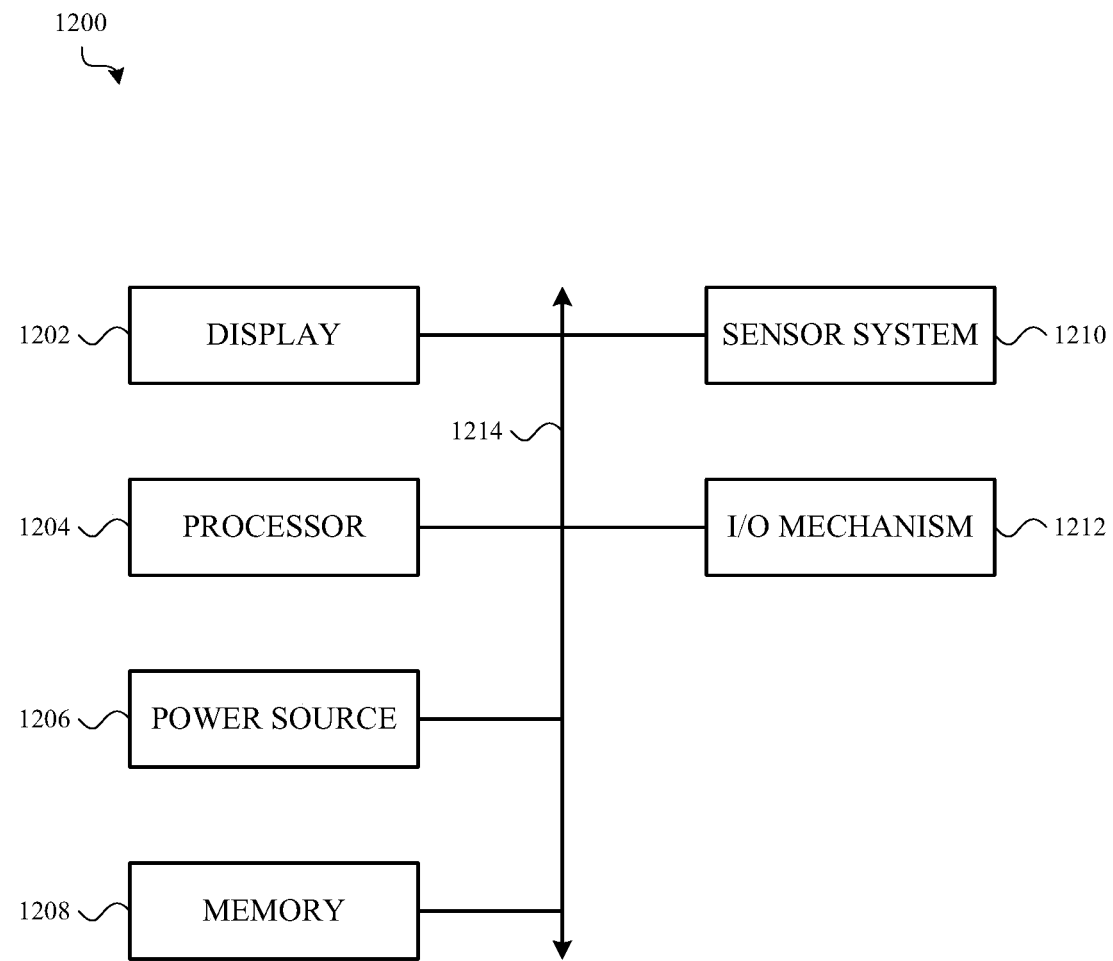
FIG. 12 shows an example electrical block diagram of an electronic device.

FIG. 12 shows a sample electrical block diagram of an electronic device 1200, which electronic device may in some cases be the stylus or wearable device described with reference to FIG. 1A or 1B, or a remote device (e.g., a mobile device or computer) that is in communication with the stylus or wearable device described with reference to FIG. 1A or 1B. The electronic device 1200 may optionally include an electronic display 1202 (e.g., a light-emitting display), a processor 1204, a power source 1206, a memory 1208 or storage device, a sensor system 1210, and/or an input/output (I/O) mechanism 1212 (e.g., an input/output device, input/output port, or haptic input/output interface). The processor 1204 may control some or all of the operations of the electronic device 1200. The processor 1204 may communicate, either directly or indirectly, with some or all of the other components of the electronic device 1200. For example, a system bus or other communication mechanism 1214 can provide communication between the electronic display 1202, the processor 1204, the power source 1206, the memory 1208, the sensor system 1210, and the I/O mechanism 1212.

The processor 1204 may be implemented as any electronic device capable of processing, receiving, or transmitting data or instructions, whether such data or instructions is in the form of software or firmware or otherwise encoded. For example, the processor 1204 may include a microprocessor, a central processing unit (CPU), an application-specific integrated circuit (ASIC), a digital signal processor (DSP), a controller, or a combination of such devices. As described herein, the term "processor" is meant to encompass a single processor or processing unit, multiple processors, multiple processing units, or other suitably configured computing element or elements. In some cases, the processor 1204 may provide part or all of the processing system or processor described herein.

It should be noted that the components of the electronic device 1200 can be controlled by multiple processors. For example, select components of the electronic device 1200 (e.g., the sensor system 1210) may be controlled by a first processor and other components of the electronic device 1200 (e.g., the electronic display 1202) may be controlled by a second processor, where the first and second processors may or may not be in communication with each other.

The power source 1206 can be implemented with any device capable of providing energy to the electronic device 1200. For example, the power source 1206 may include one or more batteries or rechargeable batteries. Additionally or alternatively, the power source 1206 may include a power connector or power cord that connects the electronic device 1200 to another power source, such as a wall outlet.

The memory 1208 may store electronic data that can be used by the electronic device 1200. For example, the memory 1208 may store electrical data or content such as, for example, audio and video files, documents and applications, device settings and user preferences, timing signals, control signals, instructions, and/or data structures or databases. The memory 1208 may include any type of memory. By way of example only, the memory 1208 may include random access memory, read-only memory, Flash memory, removable memory, other types of storage elements, or combinations of such memory types.

The electronic device 1200 may also include one or more sensor systems 1210 positioned almost anywhere on the electronic device 1200. In some cases, the sensor systems 1210 may include one or more SMI sensors, positioned and/or configured as described herein. The sensor system(s) 1210 may be configured to sense one or more types of parameters, such as but not limited to, vibration; light; touch; force; heat; movement; relative motion; biometric data (e.g., biological parameters) of a user; air quality; proximity; position; connectedness; surface quality; and so on. By way of example, the sensor system(s) 1210 may include an SMI sensor, a heat sensor, a position sensor, a light or optical sensor, an accelerometer, a pressure transducer, a gyroscope, a magnetometer, a health monitoring sensor, and an air quality sensor, and so on. Additionally, the one or more sensor systems 1210 may utilize any suitable sensing technology, including, but not limited to, interferometric, magnetic, capacitive, ultrasonic, resistive, optical, acoustic, piezoelectric, or thermal technologies.

The I/O mechanism 1212 may transmit or receive data from a user or another electronic device. The I/O mechanism 1212 may include the electronic display 1202, a touch sensing input surface, a crown, one or more buttons (e.g., a graphical user interface "home" button), one or more cameras (including an under-display camera), one or more microphones or speakers, one or more ports such as a microphone port, and/or a keyboard. Additionally or alternatively, the I/O mechanism 1212 may transmit electronic signals via a communications interface, such as a wireless, wired, and/or optical communications interface. Examples of wireless and wired communications interfaces include, but are not limited to, cellular and Wi-Fi communications interfaces.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art, after reading this description, that many modifications and variations are possible in view of the above teachings.

As described above, one aspect of the present technology may be the gathering and use of data available from various sources, including biometric data (e.g., the surface quality of a user's skin or fingerprint). The present disclosure contemplates that, in some instances, this gathered data may include personal information data that uniquely identifies or can be used to identify, locate, or contact a specific person. Such personal information data can include, for example, biometric data (e.g., fingerprint data) and data linked thereto (e.g., demographic data, location-based data, telephone numbers, email addresses, home addresses, data or records relating to a user's health or level of fitness (e.g., vital signs measurements, medication information, exercise information), date of birth, or any other identifying or personal information).

The present disclosure recognizes that the use of such personal information data, in the present technology, can be used to the benefit of users. For example, the personal information data can be used to authenticate a user to access their device, or gather performance metrics for the user's interaction with an augmented or virtual world. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide data to targeted content delivery services. In yet another example, users can select to limit the length of time data is maintained or entirely prohibit the development of a baseline profile for the user. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. An electronic device, comprising:
    a housing;
    a set of one or more self-mixing interferometry (SMI) sensors attached to the housing and including,
        a set of one or more electromagnetic radiation emitters having a set of one or more resonant cavities and configured to emit a set of one or more beams of electromagnetic radiation; and
        a set of one or more detectors configured to generate indications of self-mixing within the set of one or more resonant cavities; and
    a processor configured to,
        characterize, using the indications of self-mixing, an optical field speckle of a target; and
        characterize, using the characterization of the optical field speckle, a surface quality of the target.

2. The electronic device of claim 1, wherein:
    the processor is further configured to,
        determine, contemporaneously with at least one of characterizing the optical field speckle or characterizing the surface quality, and using the indications of self-mixing, at least one of,
            a posing of the housing with respect to the target;
            a distance of the housing to the target; or
            a velocity of movement between the housing and the target.

3. The electronic device of claim 1, wherein the processor is configured to characterize the optical field speckle by:
    performing a time domain analysis of the indications of self-mixing;
    performing a frequency domain analysis of the indications of self-mixing; and
    determining, from at least one of the time domain analysis or the frequency domain analysis, at least one of:
        an optical field speckle contrast;
        a phase shift; or
        an optical field speckle correlation length.

4. The electronic device of claim 1, wherein:
    the set of one or more SMI sensors includes at least a first SMI sensor and a second SMI sensor having different,
        angles of incidence;
        numerical apertures;
        working distances;
        polarizations; or
        emitted electromagnetic radiation wavelengths.

5. The electronic device of claim 1, further comprising:
    a set of optics disposed over an SMI sensor in the set of one or more SMI sensors; wherein,
    the processor is configured to tune the set of optics, the tuning providing diversity in the indications of self-mixing.

6. The electronic device of claim 1, wherein characterizing the surface quality comprises determining at least one of:
    surface roughness;
    surface waviness;
    subsurface scattering within the target; or
    a refractive index of the target.

7. The electronic device of claim 1, further comprising:
    a motion sensor; wherein:
        the processor is further configured to characterize the surface quality responsive to an output of the motion sensor.

8. The electronic device of claim 1, wherein:
    the housing defines a stylus body having a tip;
    the set of one or more beams of electromagnetic radiation has a set of one or more known relationships to the tip; and
    the processor is further configured to characterize the surface quality of the target using the set of one or more known relationships.

9. The electronic device of claim 1, wherein:
    the housing defines a wearable device; and
    at least a subset of the set of one or more beams of electromagnetic radiation is directed outward from an exterior of the wearable device.

10. The electronic device of claim 1, wherein:
    the housing defines a wearable device; and
    at least a subset of the set of one or more beams of electromagnetic radiation is directed inward from an interior of the wearable device.

11. The electronic device of claim 1, wherein the surface quality comprises a surface roughness.

12. The electronic device of claim 1, wherein the surface quality comprises a grain height and at least one of a grain width or a grain spacing.

13. The electronic device of claim 1, further comprising:
    a set of optics; wherein,
    an SMI sensor in the set of one or more SMI sensors,
        emits a beam of electromagnetic radiation from a resonant cavity and into the set of optics; and
        receives a returned portion of the beam of electromagnetic radiation from the set of optics and into the resonant cavity; and
    the emitted beam of electromagnetic radiation and the returned portion of the beam of electromagnetic radiation have non-reciprocal optical paths through the set of optics.

14. A method, comprising:
    receiving indications of self-mixing from a set of one or more self-mixing interferometry (SMI) sensors;
    determining, using the indications of self-mixing, at least one of a distance or a directional velocity with respect to a target;
    characterizing, using the indications of self-mixing and the at least one of the distance or the directional velocity, an optical field speckle of the target; and
    characterizing, using the characterization of the optical field speckle, a surface quality of the target.

15. The method of claim 14, further comprising:
    rendering a stroke on a display in accord with the surface quality.

16. The method of claim 14, further comprising:
    animating, in an augmented reality or virtual reality environment, an interaction between a virtual object and the target; wherein,
    the animating is performed responsive to the surface quality of the target.

17. The method of claim 14, further comprising:
    causing an actuator to provide, to a user, feedback indicative of the surface quality.

18. The method of claim 14, further comprising:
    causing an actuator to provide, to a user, feedback that masks the surface quality.

19. A method of characterizing surface quality, comprising:

receiving indications of self-mixing from a set of one or more self-mixing interferometry (SMI) sensors;

characterizing, using the indications of self-mixing, an optical field speckle of a target; and characterizing, using the characterization of the optical field speckle, a surface quality of the target.

20. The method of claim 19, wherein characterizing the surface quality comprises determining at least one of:

surface roughness;

surface waviness;

subsurface scattering within the target; or a refractive index of the target.

* * * * *